US012745927B2

(12) United States Patent
Arnold

(10) Patent No.: US 12,745,927 B2
(45) Date of Patent: Sep. 29, 2026

(54) METHOD AND DEVICE THAT GENERATES A RESPIRATION SIGNAL

(71) Applicants: Anhui Huami Health Technology Co., Ltd., Hefei (CN); Zepp, Inc., Cupertino, CA (US)

(72) Inventor: Aiden Arnold, Comox (CA)

(73) Assignees: Anhui Huami Health Technology Co., Ltd., Hefei (CN); Zepp, Inc., Milpitas, CA (US)

( * ) Notice: Subject to any disclaimer, the term of this patent is extended or adjusted under 35 U.S.C. 154(b) by 1166 days.

(21) Appl. No.: 17/475,730

(22) Filed: Sep. 15, 2021

(65) Prior Publication Data

US 2023/0084864 A1 Mar. 16, 2023

(51) Int. Cl.

| | |
|---|---|
| ***A61B 5/11*** | (2006.01) |
| ***A61B 5/00*** | (2006.01) |
| ***A61B 5/08*** | (2006.01) |
| ***A61B 5/103*** | (2006.01) |
| ***A61B 5/113*** | (2006.01) |
| *A61B 5/024* | (2006.01) |

(52) U.S. Cl.

CPC ................ *A61B 5/113* (2013.01); *A61B 5/08* (2013.01); *A61B 5/103* (2013.01); *A61B 5/1126* (2013.01); *A61B 5/681* (2013.01); *A61B 5/7225* (2013.01); *A61B 5/743* (2013.01); *A61B 5/02438* (2013.01); *A61B 2562/0219* (2013.01)

(58) Field of Classification Search

CPC ....... A61B 5/113; A61B 5/1126; A61B 5/681; A61B 5/7225; A61B 5/743; A61B 5/08; A61B 5/0295; A61B 5/103; A61B 5/02438; A61B 2562/0219

See application file for complete search history.

(56) References Cited

U.S. PATENT DOCUMENTS

| | | | | |
|---|---|---|---|---|
| 5,280,791 A * | 1/1994 | Lavie | .................. | A61B 5/1103 600/521 |
| 7,766,841 B2 * | 8/2010 | Yamamoto | ........... | A61B 5/4806 600/534 |

(Continued)

FOREIGN PATENT DOCUMENTS

| | | | |
|---|---|---|---|
| KR | 20180117909 A * | 10/2018 | ........... A61B 5/0816 |
| WO | WO-2016110804 A1 * | 7/2016 | ............... A61B 3/16 |

OTHER PUBLICATIONS

Banville et al.; Robust learning from corrupted EEG with dynamic spatial filtering; Universit'e Paris-Saclay, Inria, CEA, Palaiseau, France; pp. 1-42 (Year: 2021).*

(Continued)

*Primary Examiner* — Aurelie H Tu

(74) *Attorney, Agent, or Firm* — Young Basile Hanlon & MacFarlane, P.C.

(57) ABSTRACT

A device comprising: at least one of an accelerometer or a gyroscope and a processor. The at least one of the accelerometer or gyroscope is capable of measuring movements related to respiration of a user of the device. The processor is configured to: receive data from at least one of the accelerometer or gyroscope related to the movements of the user; dynamically filter the data; and provide a respiratory signal regarding the respiration of the user. The data from at least one of the accelerometer or gyroscope is provided without regard to a position of the device relative to the user or a position of the user.

17 Claims, 6 Drawing Sheets

(56) References Cited

U.S. PATENT DOCUMENTS

| | | | | |
|---|---|---|---|---|
| 2011/0105915 | A1* | 5/2011 | Bauer | A61B 5/4806 600/534 |
| 2015/0164410 | A1* | 6/2015 | Selvaraj | A61B 5/316 600/509 |
| 2016/0007934 | A1* | 1/2016 | Arnold | A61B 5/1118 600/595 |
| 2016/0353996 | A1* | 12/2016 | Fink | A61B 5/0002 |
| 2018/0256096 | A1* | 9/2018 | Galeev | A61B 5/0816 |
| 2018/0333102 | A1* | 11/2018 | De Haan | A61B 5/7214 |
| 2020/0279654 | A1* | 9/2020 | Maeta | A61B 5/00 |

OTHER PUBLICATIONS

Banville et al.; Robust learning from corrupted EEG with dynamic spatial filtering; Universit'e Paris-Saclay, Inria, CEA, Palaiseau, France; pp. 1-42; May 27, 2021.

* cited by examiner

METHOD AND DEVICE THAT GENERATES A RESPIRATION SIGNAL

CROSS REFERENCES TO RELATED APPLICATION(S)

NONE.

FIELD

The teachings herein relate to a device and method of generating a respiratory signal from acceleration data collected from an accelerometer and more specifically dynamically filtering the acceleration data so that the respiratory signals are ascertainable regardless of an orientation of the device and without needing to monitor the orientation of the device.

BACKGROUND

Many portable devices have been developed in which some sensors can be used to monitor various physical conditions of the user. Some of the physical conditions that may be measured include monitoring of heart rate, glucose level, apnea, hypoxia, respiratory stress, movement of the user, anxiety, and other physiological conditions. While these devices are good at monitoring physical conditions of the wearer or user, these devices have a limited ability to accurately filter a respiratory signal from the data collected via indirect monitoring.

It would be attractive to have a device that provides a respiratory signal of a user without directly monitoring breathing from the user's mouth, nasal cavity, or both. What is needed is a device that dynamically calculates respiration of a user without directly monitoring the breaths of a user, monitoring an orientation of the user, device on the user, or a combination thereof. It would be attractive to have a device, method, or both that isolates breathing movements of a user and provides a continuous respiratory signal or respiratory output. What is needed is a device that is capable of accurately providing respiratory signals or a respiratory output with only acceleration data collected from an accelerometer.

SUMMARY

Disclosed herein are implementations of a wearable device for measuring respiratory signals of a user. The present teachings provide: a device comprising: at least one of an accelerometer or a gyroscope and a processor. The at least one of the accelerometer or gyroscope is capable of measuring movements related to respiration of a user of the device. The processor is configured to: receive data from the at least one of the accelerometer or gyroscope related to the movements of the user; dynamically filter the data; and provide a respiratory signal regarding the respiration of the user. The data from the at least one of the accelerometer or gyroscope is provided without regard to a position of the device relative to the user or a position of the user.

The present teachings provide: a device comprising: an accelerometer and a non-transitory computer-readable medium. The at least one of the accelerometer or gyroscope is in communication with a user. The non-transitory computer-readable medium comprising a program configured to: monitor, dynamically filter, determine a respiratory signal, provide a respiratory signal, and displaying. The program monitors at least one of the acceleration information or velocity information from at least one of the accelerometer or the gyroscope. The program dynamically filtering at least one of the acceleration information or the velocity information from at least one of the accelerometer or the gyroscope. The program determines a respiratory signal of the user with at least one of dynamically filtered acceleration information or dynamically filtered velocity information from at least one of the accelerometer or gyroscope without regard to a position of at least one of the accelerometer or the gyroscope or a position of the user. The program provides a respiratory signal regarding the respiration of the user based upon at least one of the dynamically filtered acceleration information or the dynamically filtered velocity information. The program displays an output based upon the respiratory signal. The present teachings provide a device that provides a respiratory signal of a user without directly monitoring breathing from at least one of the user's mouth or nasal cavity. The present teachings provide a device that dynamically calculates respiration of a user without directly monitoring at least one of the breaths of a user, monitoring an orientation of the user, or device on the user. The present teachings provide a device, method, or both that isolates breathing movements of a user and provides a continuous respiratory signal. The present teachings provide a device that is capable of accurately providing respiratory signals with only acceleration data collected from an accelerometer.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
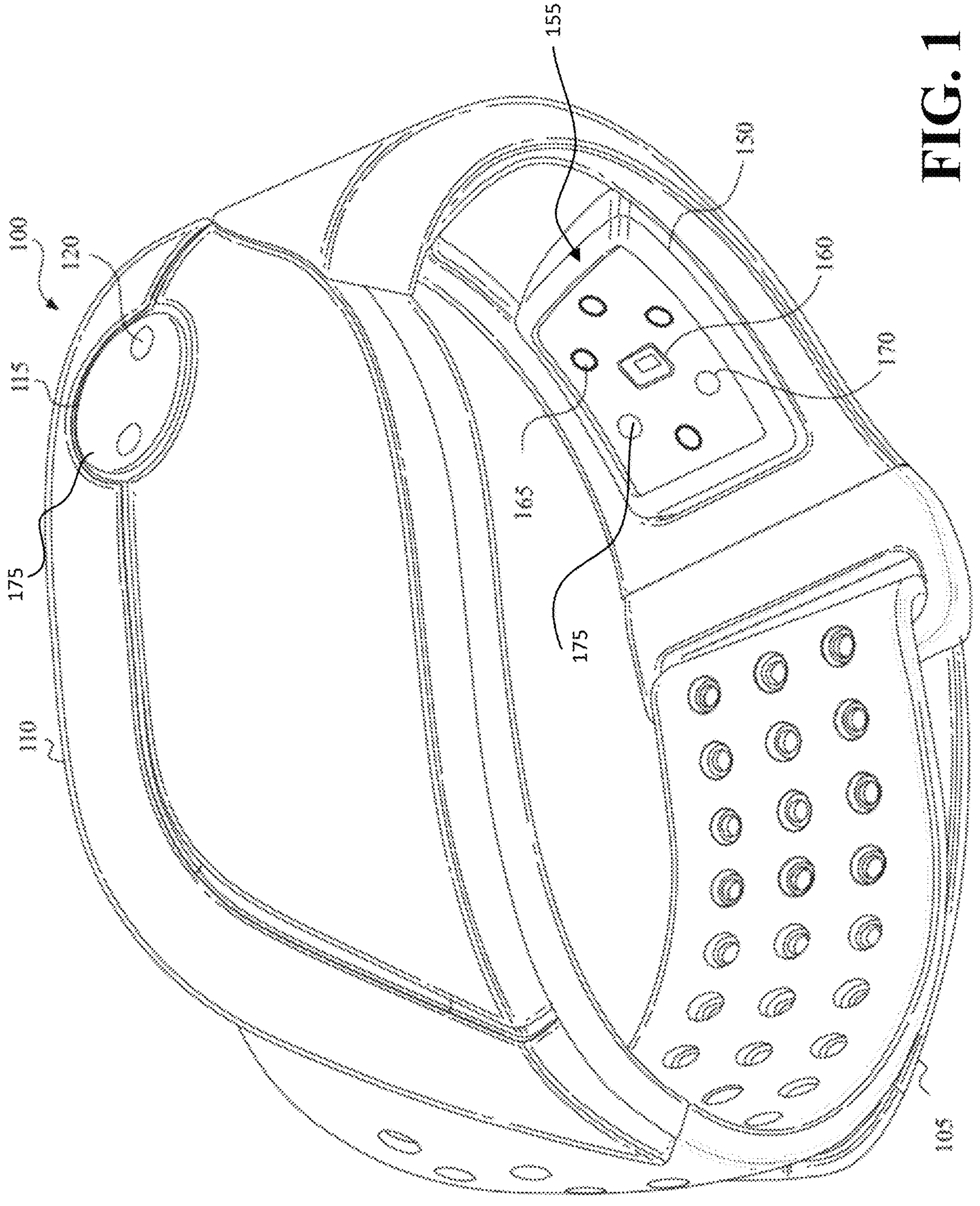
FIG. 1 depicts a device according to the teachings herein.

Example implementations will be described in detail here, and examples thereof are shown in the accompanying drawings. When the following description refers to the accompanying drawings, unless otherwise indicated, the same numerals in different accompanying drawings indicate the same or similar elements. Implementations described in the following example implementations do not represent all implementations consistent with the present application. On the contrary, they are merely examples of devices consistent with some aspects of the present application as detailed in the appended claims.

Terms used in the present application are only for the purpose of describing specific implementations, and are not intended to limit the present application. Unless otherwise defined, technical or scientific terms used in the present application shall have general meanings understood by those of general skills in the art to which the present application belongs. Similar words such as "one" or "a" used in the specification and claims of the present application do not mean a quantity limit, but mean that there is at least one. Similar words such as “including” and “containing” mean that an element or item before “including” or “containing” covers an element, item, or its equivalent listed after “including” or “containing,” and does not exclude other elements or items. Similar words such as “connect” or “connected” are not limited to physical or mechanical connections, and may include electrical connections, whether direct or indirect. “Multiple” includes two and is equivalent to at least two. Singular forms of “a,” “said,” and “the” used in the specification and appended claims of the present application are also intended to include plural forms, unless the context clearly indicates other meanings. It should also be understood that the term “and/or” as used herein refers to and includes any or all possible combinations of one or more associated listed items.

Disclosed herein is a device that senses, measures, analyzes, displays physiological information, or a combination thereof. In one aspect, the device may be a wearable device comprising at least one of an upper module or a lower module. The wearable device may be worn on a user’s body such that one or more sensors of the upper and lower modules contact a targeted area of tissue. In one implementation, the wearable device is a watch, band, or strap that can be worn on the wrist of a user such that the upper and lower modules are each in contact with a side of the wrist.

The present teachings provide a wearable device that functions to monitor physiological characteristics (e.g., a heart rate, respiration) of a user. The wearable device may monitor the physiological characteristics (e.g., a heart rate, respiration) of a user at a first location. The wearable device may monitor a first location and a second location simultaneously for physiological characteristics. For example, the wearable device may monitor a wrist (e.g., first location) of a user and a mid-section (e.g., second location) of a user. The wearable device may simultaneously measure two locations at a wrist or two locations at a waist. The wearable device may be placed at or in contact with a first location, a second location, or both in series or in parallel. For example, the wearable device may be strapped around a wrist, mid-section, or both. The wearable device may be placed proximate to a location or in contact with a location. For example, while strapped to a wrist the wearable device may be placed on a mid-section of the user so that accelerations or velocities within the mid-section of the user are measured. The physiological characteristics measured at the first location and the second location may be the same physiological characteristics or may be a different physiological characteristics. For example, the wearable device may be located on a wrist of a user (e.g., first location) and may be placed proximate to or in contact with an abdomen of a user (e.g., second location). The wearable device may be connected to a wrist and may be held against a midsection (e.g., abdomen) so that physiological characteristics of a user the user may be measured simultaneously.

The wearable device may be connected to a wrist and a portion of the device may be moved from the wrist into contact with the mid-section. The wearable device may be moved to a second location where the wearable device may monitor respiration or heart rate of the user. The wearable device may include one or more modules and the modules may be individually moved so that two separate locations may be monitored at the same time. For example, a first module may monitor at a first location and a second module may monitor at a second location. The wearable device may function to isolate one set physiological characteristics of a user from all other sets of physiological characteristics so that the one set of physiological characteristics of interest may be monitored. The physiological characteristics may be a heart rate, respiration rate, a respiration signal that may illustrate respiration of the user, or a combination thereof. The wearable device may function to isolate the respiration of the user so that a respiration signal may be displayed. The wearable device may include one or more sensors or one or more modules. The wearable device may include a plurality of modules that each include one or more sensors. The wearable device may include an upper module, a lower module, or both.

The present teachings provide a wearable device that may include a lower module that may be attached to another device. For example, the wearable device may include a lower module that is at least one of a clip or an add-on to a watch or another wearable device. For example, the lower module may be attachable to the bottom of a watch such that the lower module is in contact with the skin of the wearer. The lower module may be removable from the wearable device and may maintain communication (e.g., wireless communication) with the wearable device. The lower module may wirelessly communicate with the wearable device. The lower module may include memory that stores measurements and once reconnected the lower module synchs with the portable device. The lower module may include an accelerometer, gyroscope, or both. The accelerometer or gyroscope functions to measure movement of a user.

The accelerometer or gyroscope may measure micro-movements, macro-movements, or both. The lower module may be removable from a first location (e.g., a wrist) and placed at or on a second location (e.g., mid-section or abdomen). The lower module may be connectable to a belt or piece of clothing. The lower module may be held in place by a user’s hand. The lower module may be placed directly into contact with the mid-section or abdomen so that movements within the user may be detected (e.g., movements caused by a heartbeat or breathing). The lower module may include one or more of the sensors discussed herein. The lower module may include only an accelerometer or gyroscope. The lower module may monitor micro-movements, acceleration, velocity changes, or a combination thereof. The lower module and the upper module may include some of the same sensors. The lower module may face outward relative to the user. The lower module may be located on an opposite side of a band as an upper module. The lower module and the upper module may include some different sensors. The lower module and the upper module may monitor the same physiological characteristics and the measurements may be compared, combined, used, or a combination thereof to determine the physiological characteristics of interest.

The upper module may include one or more sensors. The sensors may monitor electrical signals of the heart, micro-movements, or both. The heart may receive electrical signals that cause the heart to beat and the sensors may monitor the electrical signals. The sensors may monitor pulse signals. The pulse signals may be movement of a part of the body caused by blood being moved through the body. The pulse signals may be movement of blood through a vein or artery. The pulse signals may monitor expansion and contraction of veins and arteries using a light. The upper module may include an optical sensor (e.g., PPG), a pulse pressure sensor (PP), a pressure sensor, an electrocardiogram (ECG), or a combination thereof. The sensors may be any device that may measure a heart rate. The optical sensors may provide a heart rate via a PPG. The sensor may provide a heart rate via a pressure sensor (PP) or ECG. The upper module may be removable from the movable device. The upper module may be fixed within the removable device. The upper module may be located opposite the lower module (e.g., 180 degrees apart). The upper module may monitor micro-movements that may be used to ascertain respiratory function (e.g., create a respiratory signal) of a user.

Each of the upper and lower modules may comprise one or more sensors, including but not limited to optical sensors (e.g., PPG), Electrocardiogram (ECG) sensors/electrodes, bio impedance sensors, galvanic skin response sensors, tonometry/contact sensors, accelerometers, gyroscopes, pressure sensors, acoustic sensors, electro-mechanical movement sensors, or electromagnetic sensors, a combination thereof. The one or more optical sensors (e.g., PPG) may comprise one or more light sources for emitting light proximate a targeted area of tissue and one or more optical detectors for detecting either reflected light (where an optical detector is located on the same side of the targeted area as the light source(s), i.e., within the same module) or transmitted light (where an optical detector is located opposite the light source(s), i.e., within an opposing module). The optical sensor may be a light emitting diode and photodiode (e.g., LED+photodiode) to measure PPG. The pressure sensor may monitor pulse pressure to provide a PP reading.

The strap or band of the wearable device may be configured so as to facilitate proper placement of one or more sensors of at least one of the upper or lower modules while still affording the user a degree of comfort in wearing the device. The present teachings may provide a strap that lies in a plane perpendicular to the longitudinal axis of the user's wrist or arm (as is the case with traditional wrist watches and fitness bands), the band may be configured to traverse the user's wrist or arm at an angle that brings one or more components of the upper or lower modules into contact with a specific targeted area of the user while allowing another portion of the band to rest at a position on the user's wrist or arm that the user finds comfortable, or around a mid-section of the user. The strap or band may be expandable so that the band is movable from a wrist to a mid-section. The strap or band may be configured to be worn during sleep so that physiological characteristics may be at least one of monitored or obtained while the user is at least one of awake or sleeping. The strap or band may be connected to another strap or band so that the wearable device may be moved from a wrist to a mid-section. For example, the wearable device may be connected to a belt extending around a mid-section of the user. The strap or band may be expandable to accommodate different body parts of a user (e.g., a wrist or a mid-section). The strap or band may be fitted around a mid-section and then a user places their wrist over the wearable device to measure the user's physiological characteristics from their wrist while physiological characteristics is being measured from the mid-section. For example, a predetermined amount of pressure may be desired to hold the wearable device on the mid-section or abdomen of the user and the strap or band may assist in creating the predetermined amount of pressure so that an accurate reading is taken. The precise location of at least one of the upper or lower modules can be customized such that one or more sensors of either module can be placed in an ideal location of a user, despite the physiological differences between body types from user to user.

The physiological characteristics sensed, measured, analyzed, or displayed can include but is not limited to heart rate information, ECG waveforms, calorie expenditure, step count, speed, blood pressure, oxygen levels, pulse signal features, cardiac output, stroke volume, respiration rate of a user, breathing movements, heart rate of a user, a respiratory signal, or a combination thereof and converted into physiological information. The physiological information may be any information associated with a physiological characteristic derived directly or indirectly from information received by one or more sensors of the wearable device. The physiological characteristics may be used in the context of, for example, health and wellness monitoring, athletic training, physical rehabilitation, patient monitoring, sleep monitoring, apnea monitoring, anxiety monitoring, asthma monitoring, or a combination thereof.

Figure 4:
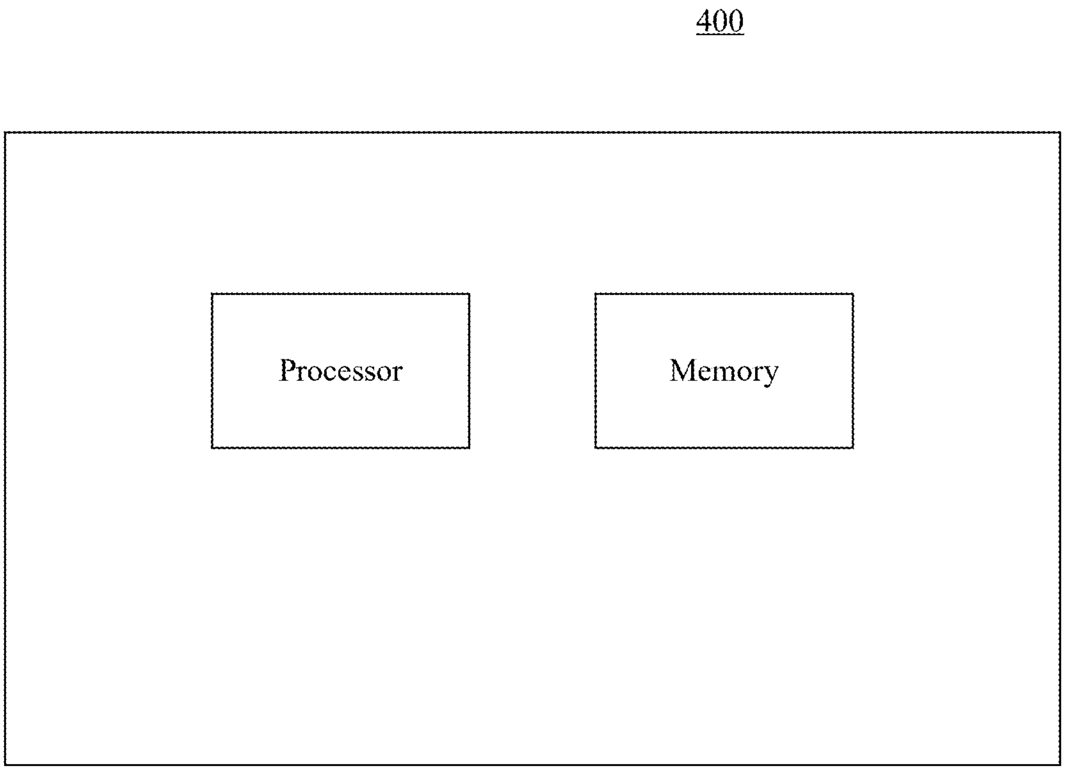
FIG. 4 depicts an example device according to some implementations of the present disclosure.

The portable device may be a wearable device (such as a wrist-worn portable device) or a hand-portable device. The portable device may include an ECG sensor (e.g., an electrode) or accelerometer that the user may place on his/her chest or other body locations. The portable device (using a processor therein as shown in FIG. 4) may detect (e.g., determine, calculate, etc.) the location of the sensor on the body to determine a lead (e.g., an angle of measurement). Preferably, the portable device is free of any detection of the position of the portable device or angle of measurement. The portable device may be free of any position sensors (e.g., a sensor that monitors a position of the portable device, a position of the portable device on a user or relative to gravity). The device may be capable of determining a position, orientation, location, or a combination thereof based upon measurements provided by at least one of the accelerometer or gyroscope. The location of the sensor may be determined using sensors of a device that is external to the portable device.

The portable device can be a wearable device that includes a strap and that can be worn on a wrist of a first arm of the user. A second sensor (e.g., an upper module or a lower module) can be included in the strap (e.g., a tail of the strap). While taking measurements, the user can touch the second sensor or hold the second sensor (such as between the thumb and index fingers of the other hand of the user or against a user's mid-section or abdomen). As such, the measurement can be more accurate when more electrodes (e.g., ECG sensors) are used. Alternatively, multiple measurements may be made of the user. The second sensor may be held by the user to determine the user's physiological characteristics while the first sensor in monitoring for different physiological characteristics. The second sensor data may be used to remove unwanted physiological information that is detected by the first sensor so that the unwanted physiological information may be removed or filtered so that physiological information of interest may be displayed.

Wrist worn ECG, PPG, PPM, or a combination thereof sensors may use a reflective system whereby a sensor array comprises one or more light sources and one or more optical detectors, located near one another and on the same side of a user's targeted area. The one or more light sources of the sensor array illuminate a portion of the user's tissue and light is reflected back to the optical detector(s) of the sensor array. The reflected light detected by the optical detector can be analyzed to estimate physiological parameters such as blood flow and pulse rate.

However, reflective systems may not be as accurate as transmissive systems that place one or more light sources on one side of a user's body and optical detectors on an opposing side of the user's body. A transmissive system may be a fingertip monitor used in a clinical setting. The monitors are clipped to a patient's fingertip, one side comprising a light source for illuminating the top or bottom of the patient's fingertip, the other side comprising an optical detector for detecting the light transmitted through the fingertip.

While the systems and devices described herein may be depicted as wrist worn devices, one skilled in the art will appreciate that the systems and methods described below can be implemented in other contexts, including the sensing, measuring, analyzing, and display of physiological data gathered from a device worn at any suitable portion of a user's body, including but not limited to, other portions of the arm, other extremities, the head, the chest, the abdomen or mid-section, or a combination thereof.

The processor functions to analyze acceleration data, velocity data, or both and to remove or isolate some of the constituents from the acceleration data, velocity data, or both. The processor may subtract, remove, isolate, or a combination thereof the first measurement from the second measurement. The processor may process data along three axes of the acceleration data, the velocity data, or both. The processor may weigh data from the acceleration data, the velocity data, or both. The respiration rates may be derived from movements (e.g., micro-movements) of a body part of a user (e.g., an abdomen, mid-section, wrist). The respiration rates may be determined by movements of the device caused by breathing movements. The respiration rates may be derived by monitoring movements of a user without knowing a position of the device relative to the user, a position of the user, or both.

Reference will now be made in detail to certain illustrative implementations, examples of which are illustrated in the accompanying drawings. Wherever possible, the same reference numbers will be used throughout the drawings to refer to the same or like items.

FIGS. 1-3B illustrate the device 100, various examples of the device 100 during use, and a flow diagram of the device 100 during use. FIG. 1 depicts a perspective view of a device 100. The device 100 may be a physiological monitor worn by a user to at least one of sense, collect, monitor, analyze, or display information pertaining to one or more physiological characteristics to provide physiological information. The device 100 comprises a band, strap, or wristwatch. The device 100 is a wearable monitoring device configured for positioning at a user's wrist, arm, another extremity of the user, or some other area of the user's body.

The device 100 may comprise at least one of an upper module 110 or a lower module 150, each comprising at least one of one or more components or sensors for detecting, collecting, processing, and displaying one or more physiological parameters and/or physiological characteristics of a user and/or other information that may or may not be related to health, wellness, exercise, or physical training sessions (e.g., characteristic information).

The upper module 110 and lower module 150 of the device 100 may comprise a strap or band 105 extending from opposite edges of each module for securing device 100 to the user. The band(s) 105 may comprise an elastomeric material or the band(s) 105 may comprise some other suitable material, including but not limited to, a fabric or metal material.

Upper module 110 or lower module 150 may also comprise a display unit (not shown) for communicating information to the user. The display unit may be an LED indicator comprising a plurality of LEDs, each a different color. The LED indicator can be configured to illuminate in different colors depending on the information being conveyed. For example, where device 100 is configured to monitor at least one of the user's heart rate or respiration rate, the display unit may illuminate light of a first color when at least one of the user's heart rate or respiration rate is in a first numerical range, illuminate light of a second color when at least one of the user's heart rate or respiration rate is in a second numerical range, and illuminate light of a third color when at least one of the user's heart rate or respiration rate is in a third numerical range. In this manner, a user may be able to detect his or her approximate heart rate and/or respiration rate at a glance, even when numerical heart rate information and/or respiration rate information is not displayed at the display unit, and/or the user only sees device 100 through the user's peripheral vision.

The display unit may comprise a display screen for displaying images, characters, graphs, waveforms, or a combination thereof to at least one of the user or a medical professional. The display unit may further comprise one or more hard or soft buttons or switches configured to accept input by the user. The display unit may switch or be toggled between displaying user physiological information.

Device 100 may further comprise one or more communication modules. Each of the upper module 110 and the lower module 150 may comprise a communication module such that information received at either module can be shared with the other module.

One or more communication modules may also communicate with other devices such as the user's cell phone, tablet, or computer. Communications between the upper and lower modules can be transmitted from one module to the other wirelessly (e.g., via Bluetooth, RF signal, Wi-Fi, near field communications, etc.) or through one or more electrical connections embedded in band 105. Any analog information collected or analyzed by either module can be translated to digital information for reducing the size of information transfers between modules. Similarly, communications between either module and another user device can be transmitted wirelessly or through a wired connection, and translated from analog to digital information to reduce the size of data transmissions.

As shown in FIG. 1, lower module 150 can comprise an array of sensor array 155 including but not limited to one or more optical detectors 160, one or more light sources 165, one or more contact pressure/tonometry sensors 170, and a at least one of an accelerometer or a gyroscope 175. These sensors are only illustrative of the possibilities, however, and lower module may comprise additional or alternative sensors such as one or more acoustic sensors, electromagnetic sensors, ECG electrodes, bio impedance sensors, or galvanic skin response, or a combination thereof. Though not depicted in the view shown in FIG. 1, upper module 110 may also comprise one or more such sensors and components on its inside surface, i.e., the surface in contact with the user's tissue or targeted area.

The location of sensor array 155 or the location of one or more sensor components of sensor array 155 with respect to the user's tissue may be customized to account for differences in body type across a group of users or placement in different locations on a user. For example, band 105 may comprise an aperture or channel within which lower module 150 is movably retained. In one implementation, lower module 150 and channel can be configured to allow lower module 150 to slide along the length of channel using, for example, a ridge and groove interface between the two components. For example, if the user desires to place one more components of sensor array 155 at a particular location on his or her wrist, or mid-section, the lower module 150 can be slid into the desired location along band 105. Though not depicted in FIG. 1, band 105 and upper module 110 can be similarly configured to allow for flexible or customized placement of one or more sensor components of upper module 110 with respect to the user's wrist or targeted tissue area.

The sensors and components proximate or in contact with the at least one of the user's tissue, upper module 110, or lower module 150 may comprise additional sensors or components on their respective outer surfaces, i.e., the surfaces facing outward or away from the user's tissue. In the implementation depicted in FIG. 1, upper module 110 comprises one such outward facing sensor array 115. The outward facing sensor array 115 may comprise one or more ECG electrodes 120, and/or one or more accelerometers and/or gyroscopes 175. Similar to the sensor arrays of the upper and lower modules proximate or in contact with the user's tissue, outward facing sensor array 115 may further comprise one or more contact pressure/tonometry sensors, photo detectors, light sources, acoustic sensors, electromagnetic sensors, bio impedance sensors, accelerometer, gyroscope, and/or galvanic skin response sensors.

The sensors of the outward facing sensor array 115 can be configured for activation when touched by the user (with his or her other hand) and used to collect additional information. The outward facing sensors may measure without being in direct contact with the user. The outward facing sensor array 115 may include at least one of an accelerometer or a gyroscope 175, which may indirectly monitor movements or micro-movements (e.g., an acceleration or a velocity change) that are transmitted to the sensor through the band or the module moving or being moved or a gyroscope that monitors velocities to determine micro-movements. In an example, where lower module 150 comprises one or more optical detectors 160 and light sources 165 for collecting ECG, PPG, or heart rate information of the user, outward facing sensor array 115 of upper module 110 may comprise ECG electrodes 120 that can be activated when the user places a fingertip in contact with the electrodes. While the optical detectors 160 and light sources 165 of lower module 150 can be used to continuously monitor blood flow of the user, outward facing sensor array 115 of upper module 110 can be used periodically or intermittently to collect potentially more accurate blood flow information which can be used to supplement or calibrate the measurements collected and analyzed by an inward facing sensor array, the sensor array 155, of lower module 150.

In addition to the inward and outward facing sensors, device 100 may further comprise additional internal components such at least one of the as one or more accelerometers or gyroscopic components for determining whether and to what extent the user is in motion (i.e., whether the user is walking, jogging, running, swimming, sitting, or sleeping), breathing rhythm, breathing signals, or a combination thereof of a user. Information collected by at least one of the accelerometer(s) or gyroscopic components can also be used to calculate the number of steps a user has taken over a period of time. This activity information can also be used in conjunction with physiological information collected by other sensors (such as heart rate, respiration rate, blood pressure, etc.) to determine a user's caloric expenditure and other relevant information. The activity information may measure movements. The movements measured may be macro-movements such as walking or jogging. The movements may be micro-movements. The micro-movements may be caused by a surface of a user's skin being moved due to respiration, heartbeat, or a both. The micro-movements may be movements of a user's mid-section. The micro-movements may have an amplitude (e.g., length) less than a predetermined amplitude in order for at least one of the accelerometer or gyroscope to at least one of the measure or record the micro-movements. For example, when a user walks the accelerometer may measure a movement of more than 1 cm, when the accelerometer detects a user heart beat the accelerometer may measure a movement of between 4 mm and 1 cm, and when the accelerometer measures a movement of 4 mm or less (e.g., a micro-movement). The micro-movements may be charted in wave form such that the micro-movements are charted with a peak and a valley. The amplitude of movement may assist the non-transitory computer readable medium or processor in isolating movements caused by multiple sources (e.g., heart beat and respiration). The processor may receive data from at least one of the accelerometer or gyroscope related to movements of the user. The processor may dynamically filter the data. The processor may provide a respiratory signal regarding the respiration of the user. The processor may analyze the data without regard to a position of the device relative to the user or a position of the user. The processor may filter out unwanted signals and isolate only desired signals. For example, the processor may learn which signals are of interest and the processor may analyze only those signals of interest. The processor may be in communication with or include a non-transitory computer-readable medium.

The non-transitory computer-readable medium may store one or more programs. The programs may be executable by the processor. The program may be configured to dynamically filter, determine a respiratory signal, provide a respiration signal, display an output, or a combination thereof. The program may control the processor to at least one of the monitor acceleration information or the velocity information from at least one of the accelerometer or the gyroscope. The program may use the processor to perform the dynamic filtering discussed herein. The program may determine a respiratory signal as discussed herein. The program may display an output as discussed herein on a device or a screen of a device as discussed herein. The program, the processor, or both may determine filter weights as discussed herein.

To determine a user's blood pressure, the PPG information described above may be combined with other sensors and techniques described herein. Determining a user's blood pressure can comprise collecting a heart rate signal using a PPG system (i.e., one or more light sources and photo detectors) and performing feature extraction (described above) on single pulses and a series of pulses. The features extracted from single pulses and series of pulses can include statistical averages of various features across a series, information regarding the morphological shape of each pulse, the average and standard deviation of morphology of a series of pulses, temporal features such as the timing of various features within single pulses, the duration of a single pulse, as well as the average and standard deviation of the timing of a feature or duration of pulses within a series of pulses, and the timing of morphological features across a series of pulses (i.e., the frequency with which a particular pulse shape occurs in a series).

As described above, this feature extraction can not only be performed on a series of pulses and single pulses, but also on portions of a single pulse. In this manner, information pertaining to both systolic and diastolic blood pressure can be ascertained as one or more portions of an individual pulse correspond to the heart's diastole (relaxation) phase and one or more other portions of an individual pulse correspond to the heart's systole (contraction) phase. In some implementations, up to 200 features can be extracted from a partial pulse, a single pulse, a series of pulses, or a combination thereof.

In addition to features extracted from PPG or ECG information, information and features can also be collected by contract/tonometry sensors, pressure sensors, bio impedance sensors galvanic skin response sensors, accelerometers, acoustic sensors, and electromagnetic sensors. For example, pressure sensors or bio impedance sensors can be used to identify blood flow pulses of user and, similar to PPG or ECG data, features can be extracted from the collected data.

When the user's extracted features are compared to features recorded in the library, device 100 can also weigh the entries of subjects most closely corresponding to the user more heavily than entries of subjects associated with indicia different from that of the user. For example, if the user is a male, features extracted from male subjects may be weighed more heavily than female subjects because a particular pulse variation in men of a particular age may correspond to relatively high blood pressure whereas the same pulse variation in women of that particular age may correspond to lower blood pressure.

According to the techniques described herein, accurate blood pressure estimates for a user can be made without requiring direct blood pressure measurement of the user. However, in some implementations, the user's blood pressure estimates can be further calibrated by direct measurement of the user's blood pressure by another device and that verified blood pressure can be input into device 100 to aid in future estimations of the user's blood pressure. Calibration can also be accomplished with an outward facing ECG sensor.

While an inward facing PPG sensor can continuously or periodically collect heart rate data of a user, occasionally the user may be prompted to place a fingertip of his or her off-hand on an outward facing ECG sensor (e.g., electrodes). The inward facing sensor arrays of device 100 may contain additional electrodes thereby completing an electrical circuit through the user's body and allowing a more precise pulse waveform to be collected. Feature extraction can be performed on these pulses, series of pulses, and partial pulses in the same manner as described above with respect to PPG information and used to cross-reference the library.

Where device 100 determines, based on its continuous or periodic monitoring of the user's blood pressure using ECG, PPG, pressure sensors, or a combination thereof that a user's blood pressure is unusually or dangerously high or low, device 100 may prompt the user to place a fingertip of an off-hand on an outward facing ECG electrode in order to verify the unusual or unsafe condition. If necessary, device 100 can then alert the user to call for help or seek medical assistance.

As described above, at least one of the upper or lower modules 110, 150 can be configured to continuously collect data from a user using an inward facing sensor array. However, certain techniques can be employed to reduce power consumption and conserve battery life of device 100. For instance, only one of the upper or lower modules 110, 150 may continuously collect information. The module may be continuously active, but may wait to collect information when conditions are such that accurate readings are most likely. For example, when one or more accelerometers or gyroscopic components of device 100 indicate that a user is still, at rest, or sleeping, one or more sensors of at least one of the upper module 110 or lower module 150 may collect information from the user while artifacts resulting from physical movement are absent. The accelerometer or gyroscope may not begin reading until the user's heart rate measured by another sensor is below a predetermined limit. For example, if the ECG, PPG, or PP demonstrates that the user is moving then the accelerometer or gyroscope may not be turned on. In another example, the accelerometer or gyroscope may turn off if macro-movements are detected or a number of macro-movements are detected above a threshold amount (e.g., 5 or more per min, 10 or more per min, 20 or more per min, 30 or more per min, or 60 or more per minute). The processor may be configured to remove or filter out macro-movements. Thus the accelerometer or gyroscope may only measure micro-movements if the macro-movements are below the threshold amount (e.g., 20 or less per minute, 10 or less per minute, 5 or less per minute, or 2 or less per minute). Thus, the accelerometer or gyroscope when set, placed, or configured to read micro-movements may only be activated when macro-movements are not present or when macro-movements are infrequent. The accelerometer or gyroscope may measure micro-movements and macro-movements simultaneously and the macro-movements may be considered an outlier and may be removed from reporting. Data provided by at least one of the accelerometer or gyroscope may include an x-component, a y-component, a z-component, or a combination of the x/y/z-components within a coordinate system.

Figure 2:
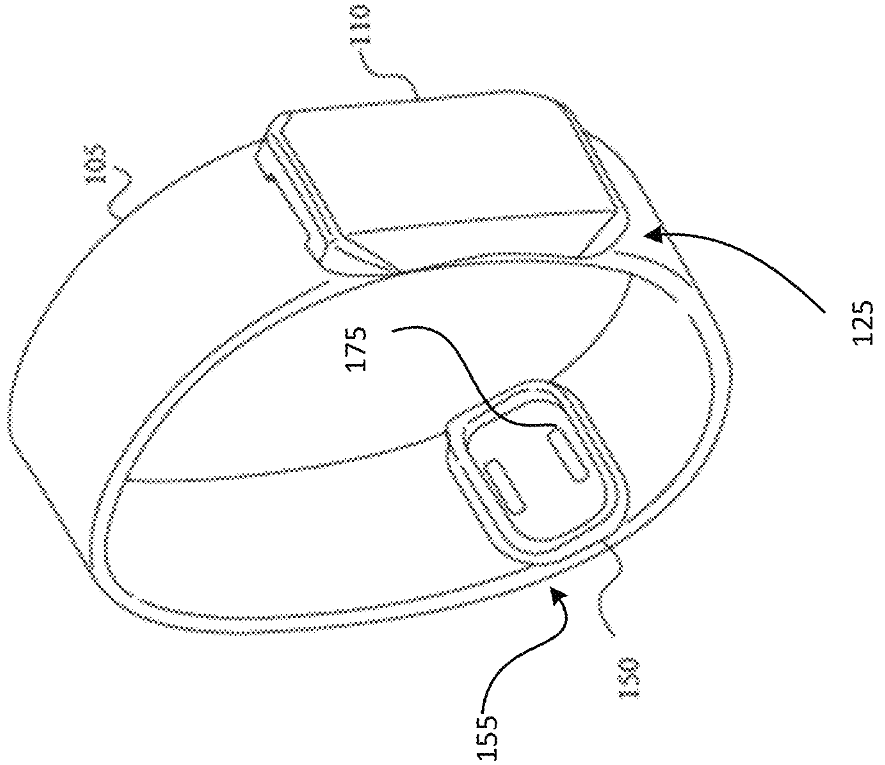
FIG. 2 depicts a device taught herein.

FIG. 2 depicts a device 100 having a band 105 and display 125 with an inward facing sensor array located opposite the display 125. The inward facing sensor array includes a sensor array 155, of lower module 150 according to the teachings herein. The sensor array 155 can comprise sensors including but not limited to one or more optical detectors, one or more light sources, one or more contact pressure/tonometry sensors, and at least one of an accelerometer or a gyroscope 175. The sensor array 155 may comprise additional or alternative sensors such as one or more acoustic sensors, electromagnetic sensors, ECG electrodes, bio impedance sensors, galvanic skin response sensors, or a combination thereof. Upper module 110 may comprise a similar inward facing sensor array configured to position sensors proximate or in contact with the outside portion of a user's wrist or arm. Sensor components of the upper module 110 and the lower module 150 can be used in combination to collect and analyze physiological information gathered by monitoring physiological characteristics. For example, one or more light sources of lower module 150 can be used to transmit light through a targeted area of the user's tissue (e.g., a portion of the user's wrist) and the transmitted light can be detected by one or more photodetectors of an inward facing sensor array of upper module 110. Opposing modules 110 and 150 can be used to detect and analyze either reflected or transmitted light.

One method for determining the heart rate, respiratory rate, blood pressure, oxygen levels, and other parameters of a user involves collecting a signal indicative of blood flow pulses from a targeted area of the user's tissue. As described above, this information can be collected using, for example, a light source, a photo detector, or a pressure sensor. Some implementations may use multiple light sources and they may be of varying colors (e.g., green, blue, red, etc.). For example, one light source may be an IR light source and another might be an LED light (such as a red LED). Using both an IR light source and a colored LED light (such as red) can improve accuracy as red light is visible and most effective for use on the surface of the skin while IR light is invisible yet effective for penetration into the skin. Such implementations may comprise multiple photo detectors, one or more configured to detect colored LED light (such as red) and one or more configured to detect IR light. These photo detectors (for detecting light of different wavelengths) can be combined into a single photodiode or maintained separate from one another. Further, the one or more light sources and one or more photodetectors could reside in the same module (upper or lower) in the case of a reflective system or the light source(s) could reside in one module while the optical detector(s) reside in the other in the case of a transmissive system.

Upon collection of a blood flow pulse signal, a number of parameters can be extracted from both single pulses and a waveform comprising multiple pulses. Features or parameters extracted from a single pulse can include, but are not limited to, shape of the pulse, a maximum amplitude, a minimum amplitude, a maximum derivative, a time difference between main and secondary peaks, and integral through the entire extraction time (i.e., the area under the pulse).

A PPG or photoplethysmogram system comprising at least one of the one or more light sources or one or more optical detectors, can be supplemented with additional sensors such as ECG electrodes/sensors, bio impedance sensors, galvanic skin response sensors, tonometry/contact sensors, accelerometers, pressure sensors, acoustic sensors, and electromagnetic sensors. For example, one or more tonometry/contact sensors can be used to extract tonometry information by measuring the contact vessel pressure. Internal facing PPG components (i.e., one or more light sources and one or more photo detectors) may be used to detect reflected or transmitted light representative of blood flow pulses and some extrapolation of the data is made to determine, for example, heart rate, the user can place a fingertip of his or her off-hand on an outward facing ECG electrode (such as that shown in FIG. 1) to collect a more precise heart rate measurement. The more precise, though of more finite duration, heart rate measurement can be used to aid in the interpretation of the continuous heart rate measurements collected by the inward facing PPG sensors. The outward facing sensor can also comprise other sensors previously described herein, such as one or more contact/tonometry sensors, one or more bio impedance sensors, and one or more galvanic skin response sensors for analyzing electric pulse response. All of the information collected by an outward facing sensor from, for example, the fingertip of the user's off-hand, can be used to refine the analysis of the continuous measurements taken by any one or more of the inward facing sensors. For example, an inward facing sensor may focus on monitoring fetal physiological information and the outward facing sensor may focus on monitoring user physiological characteristics or vice versa.

The physiological information from an upper module 110, a lower module 150, or both may be graphically displayed or represented by a waveform on the display 125. The graphical display may be provided as an output. The output may include physiological information of a user. For example, the information collected may be categorized and then graphically represented as an output or two or more outputs. The one or more outputs may be one or more waveforms, two or more waveforms, or three or more waveforms. The waveforms may be individually created. The waveforms may overlay one another. The waveforms may be created by categorizing the micro-movements. The micro-movements may be categorized by strength of the micro-movements, frequency of the micro-movements, duration of the micro-movements, or a combination thereof. The waveforms may be a one or more waveforms such as a sine wave or a sinusoidal pattern. The output may have one graph having respiration signals and a graph having a heart rate.

Techniques for estimating a user's blood pressure using pulse signal, pressure, impedance, and other collected and input information has been described above may be employed to estimate a user's oxygen levels (SpO2), hydration, respiration rate, respiration signal, and heart rate variability. For example, PPG, ECG, bio impedance, and acoustic measurements taken from the user can be cross-referenced with the aforementioned library and compared to subjects most closely matching the user (e.g., sex, age, height, weight, race, resting heart rate, BMI, current activity level, and any other medically meaningful distinction). Measured or verified hydration levels of one or more subjects can then be used to estimate the hydration level of the user. A similar process can be employed to estimate the user's oxygen levels (SpO2), respiration rate, and heart rate variability. The ECG measurements can be used to at least one of monitor or detect heart abnormalities, such as ischemia.

In a portable device, ECG sensors included in the portable device may be augmented with navigation capabilities that can aid a user in making (e.g., taking) ECG measurements or heart rate measurements at the proper places of the body (e.g., the chest, belly, mid-section). While not shown in the figures, such as for example FIG. 2, the portable device may include at least one second ECG sensor. The at least one second ECG sensor can be included in one of the lateral sides of the portable device (referred to herein as "side sensors") so that when the user is holding the portable device between the fingers, at least one of the fingers is in contact with the at least one second ECG sensor. The lateral sides of the portable device are, for example, those sides that are generally perpendicular to the side that includes the first ECG sensor. The portable device may include two accelerometers, gyroscopes, ECG sensors, or a combination thereof so that one may be located on a first side of an abdomen and the second on a second side of the abdomen or the wrist and the results compared, averaged, verified, calibrated, or a combination thereof.

The portable device may include one side sensor. The portable device includes two side sensors. The two side sensors can be placed on adjacent lateral sides of the portable device. The side sensors can be placed on opposing lateral sides of the portable device. The portable device can include a second sensor (e.g., ECG sensor) that is disposed in a side that is opposite (i.e., referred to herein as the "front sensor") the side that includes the first sensor (e.g., ECG sensor). Thus, for example, while the user is holding the portable device between users fingers, such as the thumb and the middle finger, the user can place the index finger on the front sensor. The portable device can include the first ECG sensor, at least one side sensor, and a front sensor. The portable device can include the first ECG sensor, at least two side sensors, and a front sensor. In another example, the first sensor and second sensors may be accelerometers and may be located on opposite sides of at least one of an abdomen or wrist and while the first sensor, the second sensor, or both are taking measurements the user may take a measurement with the ECG sensor.

The portable device may be a wrist-worn device, which the user can place on the user's chest, mid-section, waist, or a location therebetween while the portable device is worn by the user. The first ECG sensor can be included in a lower module, such as the lower module 150 of FIG. 1. The ECG sensor can be disposed on a side of the lower module that is opposite the side that includes the sensor array 155. The first ECG sensor is included in the side that does not face (e.g., touch, etc.) the wrist of the user. In another example, the portable device may not include a lower module. Thus, the first ECG sensor can be included (e.g., disposed, etc.) in a buckle of the strap of the portable device.

The portable device can include at least one second ECG sensor. The portable device can include a first second ECG sensor in the sensor array 155 and a second second ECG sensor in an upper module, such as the upper module 110 of FIG. 1. Thus, when taking a measurement, the user can place the first ECG sensor on his/her chest, the first second ECG sensor can touch the wrist of the user, and the user can place a finger on the second second ECG sensor.

The portable device can include at least one second ECG sensor (e.g., in a lower module 150) in the strap (e.g., a tail), such as the strap or band 105, of the portable device (referred to herein as a strap sensor). For example, the strap sensor may be disposed in a tail of the strap. The tail can be long enough so that the at least one second ECG sensor can be accessible to the user while the wrist of the user is placed on the chest. The user may wear the portable device on a right/left wrist, and as the user places an opposing hand (e.g., the right/left wrist), the user can hold the at least one second ECG sensor between the thumb and index fingers of the other left/right hand. The portable device can be configured to be worn on a wrist of a first arm of the user, the tail of the strap can include a second ECG sensor, and the second ECG sensor can be configured so that the user can hold the second ECG sensor using fingers of the second arm of the user.

The at least one second ECG sensor or accelerometer can be disposed on the strap of the portable device or in a lower module 150. The at least one second ECG sensor can be disposed on one side of the lower module. The at least one second ECG sensor can be disposed on the strap on both sides of lower module. As such, the at least one second ECG sensor can include at least two strap sensors, which the user can touch while the lower module is placed on the chest or other parts of the user's body.

The portable device may include navigation sensors. Any number of one or more navigation sensor may be used. Examples of navigation sensors include, but are not limited to, LEDs and photodiodes, an array of photosensors (e.g., minicameras, an optoelectronic sensor) with optional additional light(s), a mechanical sensor with a rolling (e.g., track) ball, or an ultrasound sensor.

For example, a mechanical sensor with a rolling ball, the rolls (e.g., movements, etc.) of the track ball can be converted to an angle and a distance of displacement on the body. For example, with respect to the optoelectronic sensor, successive images of the surface of the chest on which the portable device is moved are taken by the optoelectronic sensor to determine the angle and distance of displacement. Differences between the successive images are used to determine the displacement. For example, in the case of LEDs and photodiodes, several (e.g., 200, more, or fewer) measurements of the white level at one point can be taken and based on changes in the level of luminosity, the displacement can be determined. For example, with respect to an ultrasound sensor, differences between the successive sound reflections are can be to determine the displacement. That is, in the case of an ultrasound transceiver and receiver, several (e.g., 200, more, or fewer) measurements of the sound reflections at one point can be taken, and based on changes in the intensity of reflection (e.g., the echo), the displacement can be determined.

The navigation sensors can be or can include an accelerometer. Accelerometer data can be used to determine a displacement from a previous location to a current location of the portable device on the body of the user. A gyroscope may be additionally be used.

The displacement can be determined using a device that is external to the portable device. The external device can be a device that is in communication with the portable device. The external device can be, for example, a mobile phone or the like, of the user and that is in communication with the portable device. When the user is ready to take ECG measurements, the external device is placed by the user in front of the user so that the external device (e.g., sensors therein) can perceive the location of the portable device on the body of the user.

The portable device and the external device can communicate via wired or a wireless connection. A wired connection can be a Universal Serial Bus (USB) connection, a firewire connection, or the like. A wireless connection can be via a network using Bluetooth communications, infrared communications, near-field communications (NFCs), a cellular data network, or an Internet Protocol (IP) network. In an example, the external device can communicate the location of the portable device on the body of the user to the portable device. The portable device may receive raw sensor data from the external device and the portable device can process the raw sensor data to determine a location of the portable device on the body of the user and/or a displacement of the portable device.

The external device can include a camera, which can be used to take images of the placement of the portable device on the body of the user. Image processing can be used to determine the displacement of the portable device between a first image and a second image. Image processing may be used to determine a current location of the portable device on the body of the user.

The user can be prompted to place the ECG sensor at a reference point of the body. The reference point can be used as the initial reference point for calculating subsequent displacements for identifying the locations of the portable device on the body. The user may be prompted to move the portable device from a first location to a second location (e.g., onto a unique and easily identifiable location on the body, such as above the navel). The reference point may allow the device to auto calibrate by being placed in predetermined positions for a pre-determined amount of time. The reference points may allow for calibration of the device so that the device may determine movements without knowing (e.g., requiring knowledge of) an orientation of the device, the person, or both. The reference point may be a wrist, abdomen, chest, leg, or a combination thereof.

The user may be notified with a success signal (e.g., a sound, a haptic tap, a vibration, etc.) that the measurement at the current location is completed. The portable device can notify the user that the measurement was not successful with a failure signal. The measurement may not be successful because, for example, the ECG shape was not recognized in the signal that is received from the first ECG sensor. The ECG shape can be said to be recognized when the ECG shape matches stored normal or ischemic ECG shapes. The portable device may notify the user that the point of the measurement was not recognized.

A system for measuring an electrocardiogram (ECG) of a user includes a portable device that includes a first ECG sensor and an external device that is communication with the portable device. The portable device can include instructions stored in a memory to obtain a first ECG measurement at a first location of a body of the user, identify the first location based on sensor information received from the external device, prompt the user to move the portable device to a second location of the body of the user, and obtain a second ECG measurement at the second location of the body.

Figure 3A:
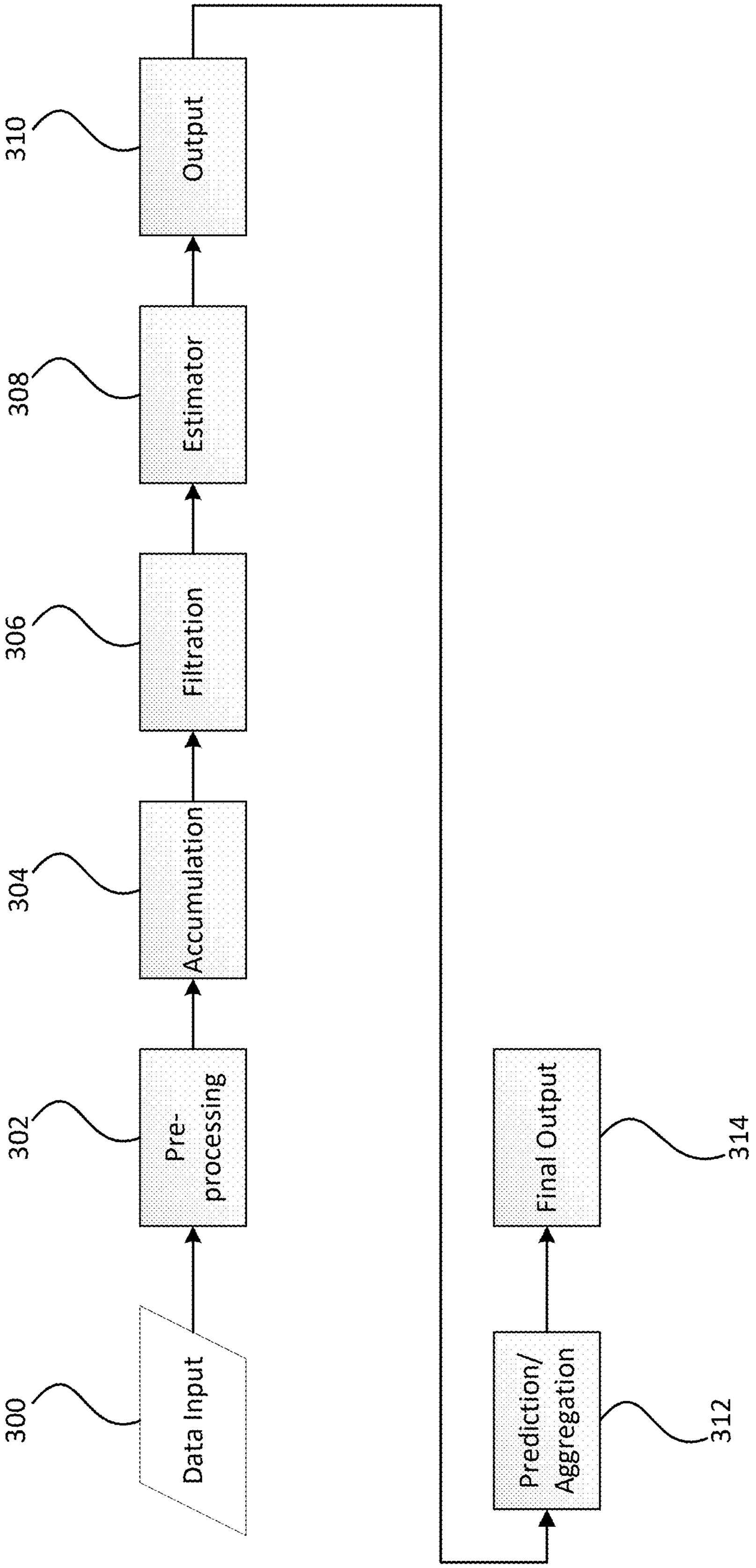
FIG. 3A depicts a flow diagram of the teachings herein processing data.

FIG. 3A illustrates a flow diagram illustrating data collection and analysis to provide a respiration signal with the device 100 taught herein in FIGS. 1 and 2. Data 300 can be provided from the at least one of the accelerometer or the gyroscope 175 of FIG. 1 or 2. The data 300 is optionally preprocessed 302 to normalize all of the data 300. The data 300 may be based upon acceleration events, velocity events, movements within a pre-determined event, micro-movements, or a combination thereof. The data 300 may monitor in or along a single axis; in or along two axes; in or along all three axes; in, along, and between all three axes; or a combination thereof. The data 300 may measure an inhale, an exhale, or both. The data 300 may be indicative of an inhale, an exhale, or both. The preprocessing 302 may remove outliers, remove redundancies, remove irrelevant data, or a combination thereof. The data 300 may be accumulated 304.

Figure 5:
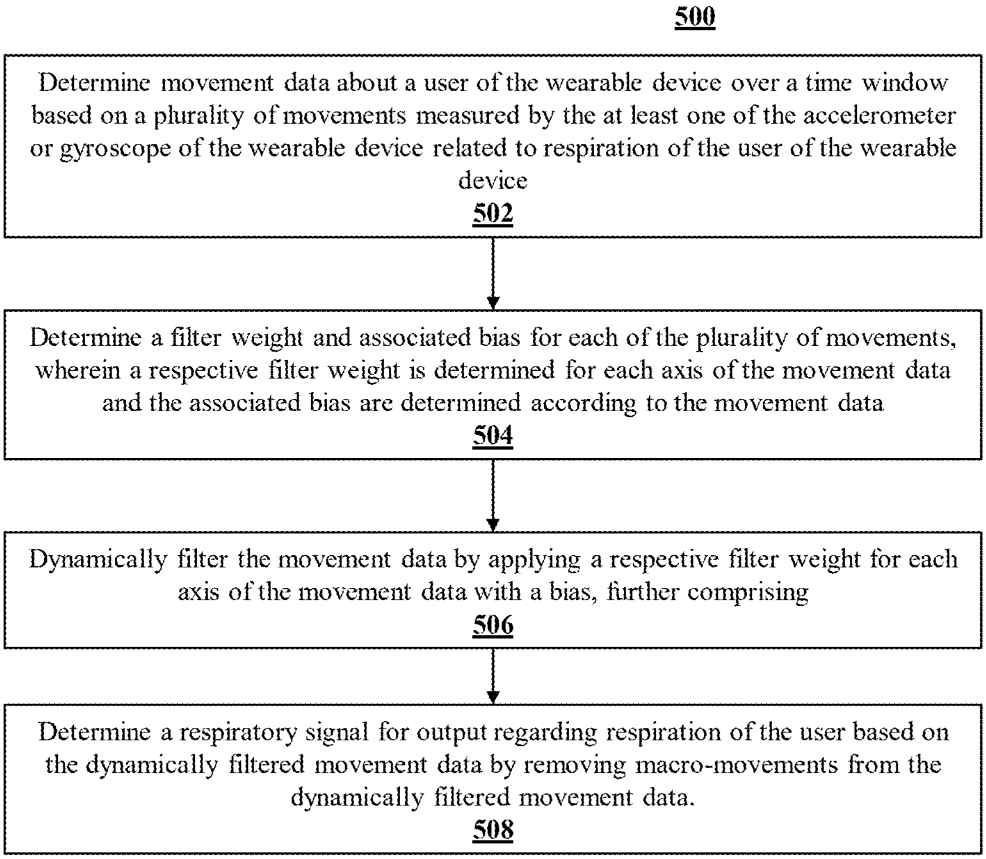
FIG. 5 is a flowchart of an example method for detecting motion-related respiratory signal according to some implementations of the present disclosure.

The accumulation 304 may accumulate all of the data along each of the three axes of at least one of the gyroscope or accelerometer. The accumulator 304 may buffer time points. For example, the accumulator 304 may buffer "n" time points. The number of time points may relate to a desired number of seconds multiplied by a sampling frequency. The buffering of the accumulation 304 may be used to calculate a covariance matrix, where each cell in the matric contains the covariance of the signal over the time window between any two of the x, y, z axes. See Table 1 below for an example of a covariance matrix. The diagonal of the matrix may be the covariance of one axis within itself, which equates to the maximal covariance value of the matrix. The accumulation 304 may allow the dynamic filter to evaluate the signal-to-noise ratio over a period of time such as 1 second and then denoise the data based on shared patterns of signals or noise across the x, y, z, axes. In an example, data is accumulated into a buffer of n×sampling frequency and the buffered data is used to calculate the covariance matrix, wherein n is the number of buffered time points, representative of n (number of) seconds in this example. The covariance matrix is converted from a matrix (e.g., 330) to a vector (e.g., 332) shown in FIG. 3B and the vector is an output to a filtration process 306. The data 300 that has been accumulated 304 may be filtered in the filtration process 306 as discussed in FIG. 3B. FIG. 5 is a flowchart of an example method for detecting motion-related respiratory signal according to some implementations of the present disclosure. At 502, movement data about a user of the wearable device over a time window is determined based on a plurality of movements measured by the at least one of the accelerometer or gyroscope of the wearable device related to respiration of the user of the wearable device, which is further illustrated in conjunction with FIGS. 1 and 2 as well as FIG. 3B below.

The filtration process 306 may be a dynamic filtering process that filters the data 300 dynamically. The filtration process 306 may filter based upon a signal-to-noise ratio. The filtration process 306 may use a machine learning model such as a convolutional neural network or other neural network architecture such as a multi-layer perceptron. The filtration process 306 may remove noise from the data 300. The filtration process 306 may filter based upon a coordinate system, movements sensed by the accelerometer or gyroscope, or both. The filtration process 306 may filter the data within a coordinate system, regardless of position, or both. The filtration process 306 may send the filtered data to the estimator 308.

The estimator 308 considers the filtered data and removes any outliers within the data from a dynamic filter of the filtration process 306. The estimator 308 may remove any abnormal events. For example, if a macro-movement exists in the respiration data, the macro-movement may be removed so that the macro-movement is not included in a respiration signal. The estimator 308 may estimate a position of a user based upon the dynamically filtered data. The estimator 308 may estimate a type of breathing, a breathing signal, or both of a user. The estimator 308 then provides an output 310. Back to FIGS. 5, 504 and 506 are illustrated in conjunction with FIG. 3B below.

The output 310 may be dynamically filtered data that dynamically weighs the acceleration or velocity changes within a coordinate system (e.g., an X component, a Y component, and a Z component). The output 310 may be a combination of data within the coordinate system that is weighted upon movements of the user (e.g., a single number that is derived from the X component, the Y component, and the Z component). The output 310 may be provided irrelevant of the location or position of the device on a user or a position of the user. The output 310 may be filtered data that is multiplied by a constant. The output 310 may be provided irrelevant of a position of the user or a position of the device. The output 310 may be provided to a step of at least one of prediction or aggregation 312.

The at least one of prediction or aggregation 312 may determine a type of breathing, a respiration signal, or both that a user is performing. The at least one of prediction or aggregation 312 may group the different outputs 310 into a single number. For example, the output 310 may have an X component, a Y component, and a Z component and at least one of the prediction or aggregation 312 may combine the three components into a single component or number. The at least one of the prediction or aggregation 312 may remove outliers, create a single signal, or both. The at least one of the prediction or aggregation 312 may compare the data to known respiratory signals to predict a type of respiration being experienced (e.g., normal, apnea, hypopnea). The at least one of the prediction or aggregation 312 may determination from a respiration signal a final output 314.

The final output 314 may be a series of numbers within the coordinate system, a three-dimensional response (e.g., in the x-axis, y-axis, z-axis), a one-dimensional response (e.g., the filtered and estimated numbers may be combined into a single output), or a combination thereof. The final output 314 (e.g., datum) may be plotted over time to show a graph of a respiration signal (e.g., peaks where breaths are taken and valleys during an exhale). The final output 314 may graphically illustrate times when a user is holding their breath, having an apnea, having a hypopnea, a panic attack, other breathing irregularities, or a combination thereof. The final output 314 may only provide a response such as that breathing is normal or consult a physician. The final output 314 may verbally characterize the breathing signal and only provide a verbal response (e.g., normal, apnea, hypopnea, panic attack). The final output 314 may be illustrated on the device, displayed on the device, or both. Back to FIG. 5, 508 is illustrated in conjunction with FIG. 3B below.

Figure 3B:
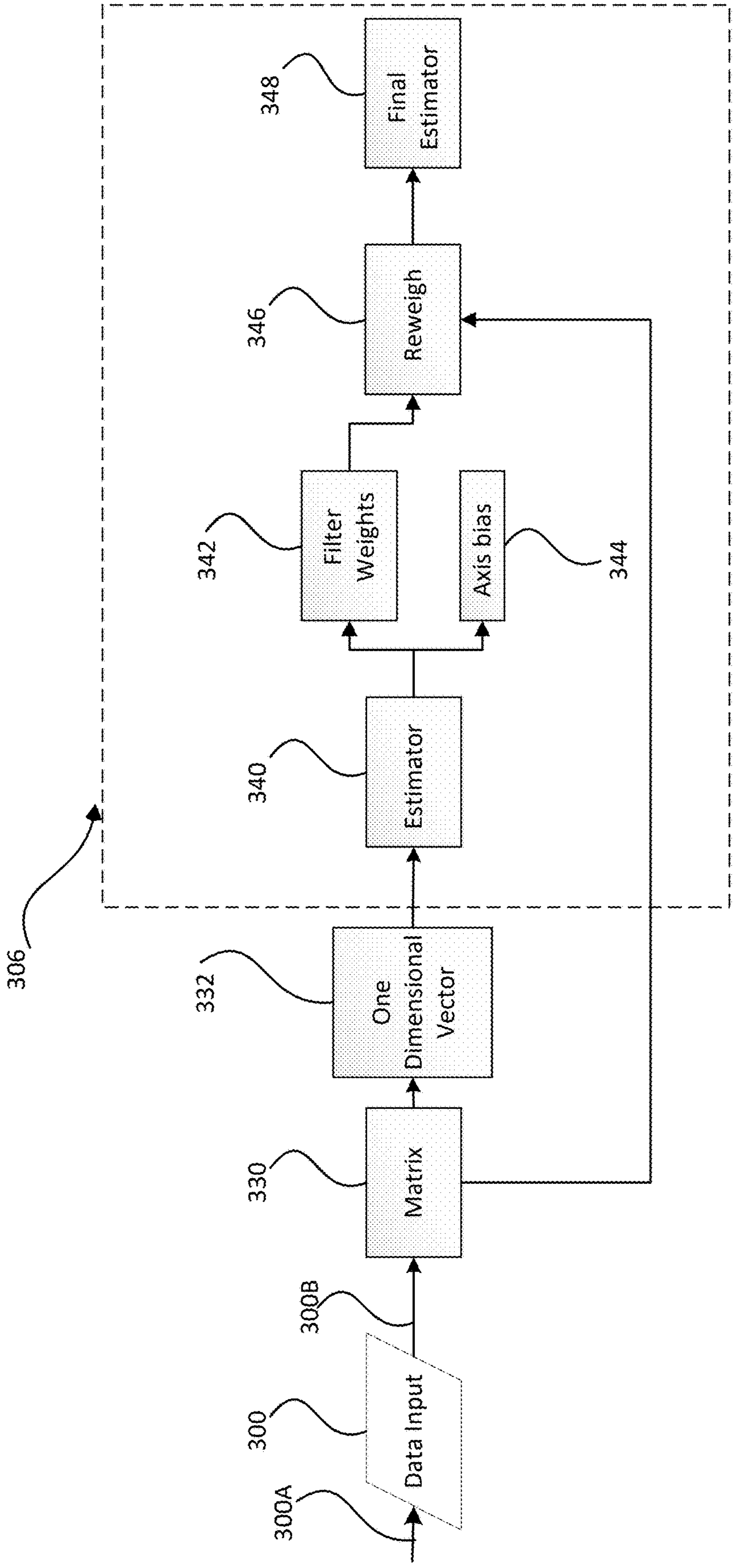
FIG. 3B depicts a portion of the flow diagram of 3A.

FIG. 3B illustrates the filtration process 306 of FIG. 3A. The data 300 input 300A from the at least one of the accelerometer or gyroscope is monitored, saved, recorded, provided to a filter, or a combination thereof. The data 300 input 300A may be provided in a matrix, converted into a matrix, may a processor or a computing device within the device, or a combination thereof. The data 300 output 300B may be in a form of a matrix 330.

The matrix 330 may be any size and shape that organizes the input data 300. The matrix may be a 3×n matrix or an n×3 matrix. The 3 may represent an X component, a Y component, and a Z component. Each of the X, Y, and Z may have its own row or column. The n may dependent upon a number of measurements over a given time. N may be 1 or more, 2 or more, 3 or more, 4 or more, 5 or more, 6 or more. N may be 100 or less, 75 or less, 50 or less, 25 or less, or 10 or less. The matrix 330 may be a 3×3 matrix. The matrix 330 may have x, y, and z along a bottom (or x-axis) and x, y, z along a side (or y-axis). Each matrix 330 may provide data per unit time. For example, if a measurement is taken every micro-second then every micro-second a matrix 330 may be formed with data from at least one of the accelerometer or gyroscope. The matrix 330 may provide data about movements within the coordinate system. The matrix 330 may record an acceleration, a velocity, a distance, or a combination thereof. For example, the matrix may be constructed as follows:

TABLE 1

| | | |
|---|---|---|
| 1 | 2 | 3 |
| 4 | 5 | 6 |
| 7 | 8 | 9 |
| X | Y | Z |

For example, square 1 illustrates an x component and a z component; square 2 represents a z component and a y component; and square 3 represents a z component and a z component. Continuing the example, square 4 illustrates a y component and an x component, square 5 represents a y component and a y component, and square 6 represents a y component and a z component. Turning to the third row of the example, square 7 has two x components, square 8 has an x component and a y component, and square 9 includes an x component and a z component. The matrix 330 may be converted to a one-dimensional vector 332 and then inputted into an estimator 340 or the matrix 330 may be directly fed into the estimator 340. The one-dimensional vector 332 may incorporate all of the numbers from the matrix 330 into a single column. The one-dimensional vector 332 may provide all of the data to the estimator 340 in a manner irrelevant of spatial position or in a manner indicative of spatial portion. The one-dimensional vector 332 may be an optional step. The one-dimensional vector 332 or the matrix 330 may be fed into the estimator 340.

The estimator 340 functions to learn the representation from the data input and select or combine the numerical representation along the axes to estimate a respiration signal. The estimator 340 functions to weigh each of the orientations within the coordinate system to determine a respiration signal. The estimator 340 may calculate a filter weight 342 for each of the measurements. For example, if 1 measurement is taken every second the 60 matrices 330 or one-dimensional vectors 332 may be inputted into the estimator 340 to determine the filter weight 342 for each measurement. For example, the x-axis may be given a weight of 0.2, the y-axis may be given a filter weight of 0.1, and the z-axis may be given a filter weight of 0.7.

The filter weights 342 function to provide an amount of influence an axis has on determining a respiration signal. The filter weights 342 may total 1, 100, 100 percent, or a combination thereof. As can be seen, the filter weights 342 may be a whole number, a percentage, a fraction of an integer, a floating number, or a combination thereof. The filter weights 342 may determine which component of the matrix 330, the one-dimensional vector 332, or both are given the most weight over determining a respiration signal. The filter weights 342 may be scaled or offset by a bias, a constant, an axis bias 344 determined for each axis of movement, or a combination thereof.

The bias, constant, axis bias 344 (hereinafter axis bias), or a combination thereof may be a constant that is applied to every component (e.g., channel) of the matrix 330, one-dimensional vector 332, or both. The axis bias 344 may increase an amplitude of the respiratory signal, cause a phase shift to the respiratory signal, shift the respiratory signal up, shift the respiratory signal down, normalize the respiratory signal, or a combination thereof. The axis bias 334 may function to provide a linear path of the respiratory signal. The axis bias 344 may be constant among all measurements. The axis bias 344 applied may vary from measurement to measurement. The axis bias 344 may be determined by the estimator 340 based upon data from at least one of the matrix 330 or one-dimensional vector 332. The axis bias 344 may change over a unit time. The axis bias 344 may change as the filter weights 342 change. Once the axis bias 344 and the filter weights 342 are determined the data from at least one of the matrix 330 or the one-dimensional vector 332 are reweighed 346. Back to FIG. 5, at 504, a filter weight and associated bias for each of the plurality of movements are determined, wherein a respective filter weight is determined for each axis of the movement data and the associated bias are determined according to the movement data.

During reweighing 346 the filter weight 342 and the axis bias 344 are applied to the data. In reweighing 346 the original data is filtered and then applied to the axis bias 344 to normalize the data. Reweighing 346 may be applied to raw data, data in the matrix 330, or data in the one-dimensional vector 332. Reweighing 346 may be applied to each of the x-component, y-component, and the z-component (e.g., three channels). Reweighing 346 may be applied to an x/y-component and an x/z-component; an x/y-component and a y/z-component; an x/z-component and a y/z-component; or a combination of two of the components (e.g., two channels). The reweighing 346 may be applied to the x/y/z-components all together (e.g., one channel). Reweighing 346 may create a virtual signal that is then normalized by the axis bias 344 to create a graphical depiction, provide a final estimation 348, or both. Reweighing 346 may weigh the data so that the output equals 1, 100%, 100, or a combination thereof. Once the reweighing 346 occurs, the output is subjected to an axis bias 344 and then provided to the final estimator 348.

The final estimator 348 may view each of the channels or components to determine if a pattern is present if an error is present, if the signal may be indicative of a condition, or a combination thereof. The final estimator 348 may determine if the respiratory signal is normal of if the respiratory signal may have some condition present. The final estimator 348 may refer a user to see a doctor, indicate an apnea, indicate a panic attack, indicate asthma, indicate hypopnea, indicate a sleep disturbance due to respiration difficulties, or a combination thereof. The final estimator 348 may provide a number score. The number score, for example, may be from 0 to 100 where 0 is normal and 100 is abnormal, and based upon the number the user is informed of a potential sleep disorder. Back to FIG. 5, at 506, the movement data is dynamically filtered by applying a respective filter weight for each axis of the movement data with a bias, which may include, for example, applying the respective filter weight for each axis of the movement data with the bias; adjusting the filter weights and the associated bias for each axis of each measurement of the movement data; and filtering the movement data by reweighing the movement data using the adjusted filter weights and the associated bias.

The device taught herein may perform a process to determine a respiratory signal or respiration types of a user. The process may be substantially embodied by FIGS. 3A-3B taught herein. The process may perform any of the steps in the order taught in FIGS. 3A-3B or in a different order. The process may not perform every step. The process my include a step of monitoring at least one of the accelerometer or gyroscope to collect movement data, information, accelerations, velocities, or a combination thereof (e.g., data). The data may be dynamically filtered. The data may be provided without regard to a position of the device relative to the user or a position of the user. The data may provide a respiratory signal. The data may supply filter weights based upon the dynamic filtering of the data. The data may be filtered. The data may be plotted. Filtered data may be plotted. Filtered data may be output. Filtered data may be reweighed. Filtered data may be compared within a coordinate system. Back to FIG. 5, at 508, a respiratory signal is determined for output regarding respiration of the user based on the dynamically filtered movement data by removing macro-movements from the dynamically filtered movement data.

It may be appreciated that various changes can be made therein without departing from the spirit and scope of the disclosure. Moreover, the various features of the implementations described herein are not mutually exclusive. Rather any feature of any implementation described herein may be incorporated into any other suitable implementation.

Additional features may also be incorporated into the described systems and methods to improve their functionality. For example, those skilled in the art will recognize that the disclosure can be practiced with a variety of physiological monitoring devices, including but not limited to heart rate and blood pressure monitors, and that various sensor components may be employed. The devices may or may not comprise one or more features to ensure they are water resistant or waterproof. Some implementations of the devices may hermetically sealed.

Other implementations of the aforementioned systems and methods will be apparent to those skilled in the art from consideration of the specification and practice of this disclosure. It is intended that the specification and the aforementioned examples and implementations be considered as illustrative only, with the true scope and spirit of the disclosure being indicated by the following claims.

While the disclosure has been described in connection with certain implementations, it is to be understood that the disclosure is not to be limited to the disclosed implementations but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A wearable device for determining a respiratory signal using motion data, comprising:

at least one of an accelerometer or gyroscope that is capable of measuring movements related to respiration of a user of the wearable device; and a processor configured to:

determine movement data about the user of the wearable device over a time window based on a plurality of movements measured by the at least one of the accelerometer or gyroscope related to the respiration of the user;

dynamically filter the movement data by applying a respective filter weight for each axis of the movement data with an associated bias, further comprising:

determining a filter weight for each axis of the movement data according to the movement data, wherein the filter weight for each axis is determined based on a covariance of the movement data over the time window between same or different axes of the movement data;

determining a signal-to-noise ratio for the covariance of the movement data over a current time window;

denoising the covariance of the movement data based on the signal-to-noise ratio according to shared patterns of signals or noises across each axis of the movement data;

filtering the movement data based on the respective filter weight for each axis of the movement data to obtain filtered movement data;

determining the associated bias for each axis of the movement data according to the filtered movement data; and normalizing the filtered movement data by using the associated bias determined for each axis of the movement data to obtain the dynamically filtered movement data; and determine a respiratory signal for output regarding the respiration of the user based on the dynamically filtered movement data by removing macro-movements from the dynamically filtered movement data without regard to a position of the wearable device relative to the user or a position of the user, wherein the respiratory signal comprises at least one of a respiration rate or a respiration type of the user, wherein the movements measured by the at least one of the accelerometer or gyroscope comprise micro-movements and the macro-movements, and the processor is configured to filter out the macro-movements when the movement data is dynamically filtered, and wherein the processor is further configured to control the at least one of the accelerometer or gyroscope by:

detecting a number of macro-movements over a time period;

when the number of macro-movements is above a threshold amount, turning off or not activating the at least one of the accelerometer or gyroscope for measuring the micro-movements; and activating the at least one of the accelerometer or gyroscope to measure the micro-movements only when the number of macro-movements is below the threshold amount.

2. The wearable device of claim 1, wherein the wearable device is free of a position sensor that provides an orientation of the wearable device on the user or a position of the user.

3. The wearable device of claim 1, wherein the movements measured by the at least one of the accelerometer or gyroscope include movement data with three axis components within a coordinate system.

4. The wearable device of claim 3, wherein the processor configured to dynamically filter the movement data by applying the respective filter weight for each axis of the movement data with the associated bias is further configured to:

apply filter weights to each axis component of the movement data with three axis components during the dynamically filtering of the movement data so that the micro-movements provide the respiratory signal without the position of the wearable device relative to the user or the position of the user being monitored.

5. The wearable device of claim 1, wherein the processor is configured to determine and output an indication of a type of breathing based upon the respiration signal.

6. The wearable device of claim 1, wherein the processor is further configured to:

determine, based on the respiratory signal, whether the respiratory signal is indicative of a medically relevant condition comprising at least one of asthma, apnea, hypopnea, panic attack, or a sleep disturbance due to respiration difficulties; and in response to determining that the respiratory signal is indicative of the medically relevant condition, display on the wearable device a graphical or verbal indication of the medically relevant condition or an indication to consult a physician.

7. A wearable device for determining a respiratory signal using motion data, comprising:

at least one of an accelerometer or gyroscope in communication with a user; and a non-transitory computer-readable medium comprising a program configured to:

determine movement data about the user of the wearable device over a current time window based on a plurality of movements measured by the at least one of the accelerometer or the gyroscope related to respiration of the user of the wearable device;

determine a filter weight and associated bias for each of the plurality of movements over the current time window, wherein a respective filter weight is determined for each axis of the movement data according to the movement data, and the filter weight for each axis is determined based on a covariance of the movement data over the current time window between same or different axes of the movement data;

dynamically filter the movement data based on a signal-to-noise ratio by applying the respective filter weight for each axis of the movement data with the associated bias, wherein the program is further configured to:

apply the respective filter weight for each axis of the movement data; and reweigh the movement data using the associated bias determined for the current time window;

determine a respiratory signal regarding the respiration of the user based on the dynamically filtered movement data by removing macro-movements from the dynamically filtered movement data without regard to a position of the at least one of the accelerometer or the gyroscope or a position of the user; and display an output based upon the respiratory signal, wherein the respiratory signal comprises at least one of a respiration rate or a respiration type of the user, wherein the movements measured by the at least one of the accelerometer or gyroscope comprise micro-movements and the macro-movements, and the program is configured to filter out the macro-movements when the movement data is dynamically filtered, and wherein the program is further configured to control the at least one of the accelerometer or gyroscope by:

detecting a number of macro-movements over a time period;

removing the macro-movements from the filtered movement data so that the macro-movements are not included in the respiratory signal;

when the number of macro-movements is above a threshold amount, turning off or not activating the at least one of the accelerometer or gyroscope for measuring the micro-movements; and activating the at least one of the accelerometer or gyroscope to measure the micro-movements only when the number of macro-movements is below the threshold amount, and removing the macro-movements from the filtered movement data so that the macro-movements are not included in the respiratory signal.

8. The wearable device of claim 7, wherein the non-transitory computer-readable medium comprising the program configured to apply the respective filter weight for each axis of the movement data is further configured to apply filter weights to each of three axis components of the movement data during the dynamically filtering of the movement data so that micro-movements monitored by at least one of the accelerometer or the gyroscope provide the respiratory signal without knowing a position of the wearable device relative to the user or the position of the user being monitored.

9. The wearable device of claim 8, wherein the non-transitory computer-readable medium comprising the program to reweigh the movement data using the associated bias determined for the current time window is further configured to reweigh the movement data from the at least one of the accelerometer or gyroscope so that a combined output of the three axis components is based upon the filter weights, and each filter weight is a whole number, a percentage, a fraction of an integer, a floating number, or a combination thereof.

10. The wearable device of claim 9, wherein the output is a plot of all of the combined outputs that are reweighed so that a graph is created that illustrates the respiratory signal.

11. A method determining a motion-related respiratory signal using a wearable device comprising at least one of an accelerometer or gyroscope, the method comprising:

determining, by the wearable device, movement data about a user of the wearable device over a current time window based on a plurality of movements measured by the at least one of the accelerometer or gyroscope of the wearable device related to respiration of the user of the wearable device, wherein the movement data further comprises covariance of the movement data derived from the plurality of movements measured over the current time window between same or different axes of movement as measured by the wearable device;

determining a signal-to-noise ratio for the covariance of the movement data over the current time window;

denoising the covariance of the movement data based on the signal-to-noise ratio according to shared patterns of signals or noises across each axis of the movement data;

determining a filter weight and associated bias for each of the plurality of movements over the current time window, wherein a respective filter weight is determined for each axis of the movement data and the associated bias according to the movement data;

dynamically filtering the movement data by applying a respective filter weight for each axis of the movement data with the associated bias, further comprising:

applying the respective filter weight for each axis of the movement data; and reweighing the movement data using the associated bias determined for the current time window; and determining a respiratory signal for output regarding respiration of the user based on the dynamically filtered movement data without regard to a position of the wearable device relative to the user or a position of the user, wherein the respiratory signal comprises at least one of a respiration rate or a respiration type of the user, wherein the movements measured by the at least one of the accelerometer or gyroscope comprise micro-movements and macro-movements, and the macro-movements are filtered out when the movement data is dynamically filtered, and wherein the method further comprises:

detecting a number of macro-movements over a time period;

when the number of macro-movements is above a threshold amount, turning off or not activating the at least one of the accelerometer or gyroscope for measuring the micro-movements; and activating the at least one of the accelerometer or gyroscope to measure the micro-movements only when the number of macro-movements is below the threshold amount.

12. The method of claim 11, further comprising: categorizing an output after the movement data is reweighed or plotting the output to form a graphical representation of the respiratory signal.

13. The method of claim 11, wherein the movement data includes movement data with three axis components within a coordinate system, and the method further comprises:

determining a numerical score for the respiratory signal regarding the respiration of the user, wherein an abnormal respiratory event is determined for the user based on the numerical score.

14. The method of claim 13, further comprising applying filter weights to each axis component of the movement data with three axis components during the dynamically filtering of the movement data so that micro-movements monitoring the at least one of the accelerometer or gyroscope provide the movement data that is converted into a respiratory signal without requiring knowledge of a position of the wearable device relative to the user or a position of the user and without the position of the wearable device relative to the user or the position of the user being monitored.

15. The method of claim 14, further comprising displaying an output demonstrating the respiratory signal.

16. The method of claim 11, wherein the covariance of the movement data is determined for a successive time window, and the filter weight and the associated bias are adjusted for each axis in response to changes in the covariance of the movement data between the current time window and the successive time window.

17. The method of claim 11, further comprising:

after denoising the covariance of the movement data, detecting macro-movements from the filtered movement data as outliers or abnormal events and;

removing the macro-movements from the filtered movement data so that the macro-movements are not included in the respiratory signal.

* * * * *